(12) United States Patent
Beaven (10) Patent No.: US 10,646,252 B2
(45) Date of Patent: May 12, 2020

(54) MEDICATION SLEEVE FOR A TROCAR ASSEMBLY

(71) Applicant: Modern Surgical Solutions, LLC, Covington, KY (US)

(72) Inventor: Richard B. Beaven, Covington, KY (US)

(73) Assignee: MODERN SURGICAL SOLUTIONS, LLC, Covington, KY (US)

( * ) Notice: Subject to any disclaimer, the term of this patent is extended or adjusted under 35 U.S.C. 154(b) by 282 days.

(21) Appl. No.: 15/915,345

(22) Filed: Mar. 8, 2018

(65) Prior Publication Data

US 2019/0274726 A1      Sep. 12, 2019

(51) Int. Cl.

| A61B 17/34 | (2006.01) |
|---|---|
| A61M 19/00 | (2006.01) |
| A61M 13/00 | (2006.01) |
| A61M 5/142 | (2006.01) |
| A61B 17/00 | (2006.01) |

(52) U.S. Cl.
CPC ......... *A61B 17/3423* (2013.01); *A61M 5/142* (2013.01); *A61M 13/003* (2013.01); *A61M 19/00* (2013.01); *A61B 17/3498* (2013.01); *A61B 2017/00893* (2013.01); *A61B 2017/3437* (2013.01); *A61M 2005/14208* (2013.01)

(58) Field of Classification Search
CPC ..... A61B 17/34; A61B 17/00; A61B 17/3423; A61B 17/3498; A61B 2017/00893; A61B 2017/3437; A61B 17/3417; A61B 17/3421; A61B 17/3474; A61B 2217/007; A61M 13/003; A61M 19/00; A61M 5/142; A61M 2005/14208

USPC .......................................................... 604/264
See application file for complete search history.

(56) References Cited

U.S. PATENT DOCUMENTS

| 4,863,457 A | 9/1989 | Lee |
| 5,618,563 A | 4/1997 | Berde et al. |
| 5,743,881 A | 4/1998 | Demco |
| 5,882,345 A * | 3/1999 | Yoon ............... A61B 17/3439 604/104 |
| 6,228,068 B1 | 5/2001 | Yoon |
| 6,248,345 B1 | 6/2001 | Goldenheim et al. |
| 6,270,484 B1 | 8/2001 | Yoon |
| 6,302,873 B1 | 10/2001 | Moenning |
| 6,695,815 B2 | 2/2004 | Moenning |

(Continued)

*Primary Examiner* — Jason E Flick
(74) *Attorney, Agent, or Firm* — Ronald J. Richter; Hasse & Nesbitt LLC (57) ABSTRACT

An obturator sleeve for a trocar assembly and method of its use are disclosed for infiltrating a liquid medication such as a local anesthetic into the tissue walls of a port site wound during a laparoscopic procedure. The sleeve includes an internal flow passage for receiving the liquid medication. A diffusion polymer, located within the internal flow passage, first absorbs the liquid medication and then releases the liquid medication through a plurality of apertures in the sleeve. When port site wound tissue contacts the diffusion polymer, the diffusion polymer within the sleeve steadily releases the absorbed medication through the plurality of apertures. The obturator sleeve provides a means to adequately infiltrate medication into the tissues of the port site wound, and can be used to block the free nerve endings of the port site wound as well as nearby sensory and motor nerves.

18 Claims, 5 Drawing Sheets

(56) References Cited

U.S. PATENT DOCUMENTS

| | | | |
|---|---|---|---|
| 7,976,858 B2 | 7/2011 | Hotchkiss et al. | |
| 8,846,068 B2 | 9/2014 | Wohabrebbi et al. | |
| 8,900,620 B2 * | 12/2014 | Fulmer | A61M 31/002 |
| | | | 424/426 |
| 9,125,902 B2 | 9/2015 | Haddock et al. | |
| 9,445,884 B2 | 9/2016 | Barron et al. | |
| 2002/0055666 A1 | 5/2002 | Hunter et al. | |
| 2005/0019613 A1 | 6/2005 | Moenning et al. | |
| 2007/0073248 A1 | 3/2007 | Moenning | |
| 2011/0238016 A1 | 9/2011 | Hotchkiss et al. | |

* cited by examiner

MEDICATION SLEEVE FOR A TROCAR ASSEMBLY

FIELD OF THE INVENTION

The present invention relates generally to the field of laparoscopic surgery, and in particular to devices and methods for delivery of a liquid medication into the tissues around a port site wound during a laparoscopic procedure.

BACKGROUND OF THE INVENTION

Laparoscopic surgery, or minimally invasive surgery, is an operation performed in the abdomen or pelvis with the aid of viewing tubes or laparoscopes. A laparoscope is typically connected fiberoptically to a video camera, which transmits the picture to a TV monitor. A plurality of small incisions (typically 0.5-1.5 cm in length) are made in the skin, through which surgical trocar assemblies or other similar puncturing devices are inserted to create "ports" traversing the abdominal wall. For example, surgical instruments can be inserted through one or more of the small ports, an air insufflation device can be inserted through a different small port, and a laparoscope for viewing can be inserted through yet another small port. Laparoscopic surgery has replaced many standard invasive abdominal surgical procedures that require large incisions. When compared to open abdominal surgery, laparoscopic technology provides decreased postoperative pain, a decreased hospital stay, shorter-term postoperative ileus, improved wound healing and mobility, smaller scars (improved cosmesis), earlier return to daily activity, decreased cost, and increased patient satisfaction.

A typical trocar assembly used to puncture the abdominal wall in laparoscopic surgery includes a central obturator and a hollow sleeve, or cannula. The obturator is typically elongate and has a sharpened distal end suitable for efficiently yet safely puncturing the layers of the abdominal wall. The hollow sleeve fittingly slides over the outer diameter of the obturator, and the two are typically used together to access the intraperitoneal space. Once the intraperitoneal space is visualized, the obturator is removed and the sleeve remains as a port or interface. The proximal or external end of the sleeve is typically attached to a hub for introducing and removing various surgical instruments therethrough. The hub is typically fitted with air insufflation components and various pneumostasis valves for sealably receiving the surgical instruments. The intraperitoneal space is typically insufflated with pressurized carbon dioxide to provide more room and better exposure for viewing the anatomy and manipulating instruments through the ports. Scissors, dissectors, retractors, and biopsy instruments can be manipulated through a plurality of surgically placed ports, together with viewing devices such as endoscopes or laparoscopes, to perform the planned surgery or diagnostic procedure.

Because of increasing medical and hospitalization costs, it is desirable to perform laparoscopic procedures on an outpatient basis. A major post-operative hurdle for laparoscopy patients, however, is "port site pain" resulting from the trauma caused by the obturator when puncturing the abdominal wall. To decrease and/or prevent post-laparoscopy port site pain, local anesthesia can be advantageously administered pre-operatively, in combination with general anesthesia during the procedure. Pre-operative local injection of anesthetics such as lidocaine and/or bupivacaine can decrease the amount of general anesthesia needed, and speed up recovery time. As a result, most current outpatient laparoscopic procedures utilize pre-operative administration of a local anesthetic. Liquid anesthetic medication is injected at the planned point of insertion of the obturator, and along the anticipated obturator wound tract through the abdominal wall. While useful if properly done, satisfactory pre-operative placement of local anesthetic into a proposed wound tract is difficult to perform by hand. The path of injection of the liquid medication is often indiscriminate and inaccurate, resulting in its application in the wrong place.

For example, injection of the skin at the proposed incision point and along the projected path of the obturator does not always place the anesthetic along the true path later traveled by the obturator through the abdominal wall. This is complicated by the fact that the obturator path typically travels at an angle relative to the skin incision. This can result in incomplete anesthesia of the "port site wound", i.e. the surgical wound created by the true path taken through the abdominal wall by the puncturing trocar assembly. Port site wound pain can lead to patient discomfort during the procedure and an increased reliance on the general anesthetic to complete the procedure. In addition, post-operative "break through pain" can result, even with accurate placement of local anesthetic, due to metabolization of the pre-operatively administered local anesthetic during the surgical procedure. This can lead to an increased reliance on post-operative narcotics and a slower recovery time.

In addition to the pre-operative administration of local anesthetic noted above, current surgical practice commonly includes the administration of local anesthetic at the conclusion of surgery, directly into the walls of the port site wound. The goal is to provide local anesthetic at maximum strength in the tissues forming the port site wound, both intra-operatively and immediately post-operatively, in order to prevent port site pain and/or break through pain. Timing can be important, because if the surgeon administers the local anesthetic too late at the end of the procedure, there may not be time for the medication to adequately take effect before the patient wakes up. Too early, and the local anesthetic effect may be gone. Either way, if the timing is off the patient may suffer immediate post-operative port site pain. Indeed, providing maximum intra- and post-operative local anesthetic effect at the tissues around the trocar wound has been difficult to accomplish.

U.S. Patent Pub. No. 2007/0073248 to Moenning discloses a trocar assembly for a laparoscopic procedure which can intra-operatively dispense a biologically active compound such as a cancer medication. The obturator sleeve includes an interior cavity connected to a fluid delivery channel at the hub, with apertures located down the length of the sleeve communicating with the internal cavity so that medication can be dispensed to the outside surface of the sleeve. While beneficial, the present inventor has found that such a trocar assembly is not always sufficient for post-operative pain relief. Notably, it has been observed that local anesthetic, which is a liquid, upon injection into the sleeve simply follows the path of least resistance and flows out of the apertures of the sleeve and into the abdominal cavity. This is potentially hazardous, since the absorption dynamics of local anesthetics such as bupivacaine into the peritoneal membranes are less predictable as compared to absorption into the tissues of the abdominal wall. This is especially true if the abdominal wall is thin, such that the apertures empty directly into the insufflated peritoneal space. In addition, since an injected liquid has a tendency to pool into the most gravity-dependent portion of the sleeve, uneven distribution of the medication within the trocar wound tract often results. If the obturator is placed into the patient at an angle, as is typically done in practice, injection of local anesthetic through the sleeve will not uniformly anesthetize the wound path.

It is apparent from the above discussion that there is a need in the laparoscopic surgical arts for more effective delivery of local anesthesia medication to the tissues surrounding a port site trocar wound. It would therefore be beneficial to provide a device and method for accurately delivering a liquid local anesthetic medication along the true path of a port site wound during a laparoscopic procedure. It would also be advantageous if such a device and method could be utilized by surgeons having a variety of different skill levels. It would also be advantageous to provide an improved means for reducing post-operative port site pain, breakthrough pain, and narcotic use, which can improve patient comfort and enhance the outpatient capabilities of laparoscopic procedures.

SUMMARY OF THE INVENTION

Accordingly, the present invention provides a means to uniformly, reliably and steadily introduce medication such as a local anesthetic into an abdominal trocar wound site during a laparoscopic procedure. The invention provides a means to deliver local anesthetic exactly along the true path of a port site wound so that the walls and surrounding tissues of the wound remain anesthetized for an extended period of time.

A first aspect of the invention provides an obturator sleeve for delivery of a liquid medication along the path of a port site wound during a laparoscopic procedure, wherein the sleeve is an elongated tube comprising: (a) a proximal end, a distal end, an outer wall, and an inner wall, the inner wall forming a hollow passage for advancement of medical instruments through the sleeve; (b) an internal flow passage for receiving a liquid medication, wherein the internal flow passage is located between the outer wall and the inner wall of the sleeve and between the proximal end and the distal end of the sleeve; (c) a medication inlet for delivery of the liquid medication to the internal flow passage, wherein the medication inlet is located at the proximal end of the sleeve and is fluidly connected to the internal flow passage; (d) a plurality of apertures located within the outer wall and opening into the internal flow passage; and (e) a diffusion polymer located within the internal flow passage for initially absorbing the liquid medication delivered into the internal flow passage and then releasing the absorbed medication through the apertures.

A second aspect of the invention provides a trocar assembly for delivery of a liquid medication along the path of a port site wound during a laparoscopic procedure, the assembly comprising: (a) an obturator for creating a port site wound by puncturing the abdominal wall of a patient undergoing a laparoscopic procedure; and (b) an obturator sleeve in the form of an elongated tube configured to fittingly slide over the obturator, the sleeve comprising: (i) a proximal end, a distal end, an outer wall, and an inner wall, the inner wall forming a hollow passage for advancement of medical instruments through the sleeve; (ii) an internal flow passage for receiving a liquid medication, wherein the internal flow passage is located between the outer wall and the inner wall of the sleeve and between the proximal end and the distal end of the sleeve; (iii) a medication inlet for delivery of the liquid medication to the internal flow passage, wherein the medication inlet is located at the proximal end of the sleeve and is fluidly connected to the internal flow passage; (iv) a plurality of apertures located within the outer wall and opening into the internal flow passage; and (v) a diffusion polymer located within the internal flow passage for initially absorbing the liquid medication delivered into the internal flow passage and then releasing the absorbed medication through the apertures, wherein the released medication infiltrates the tissues of the port site wound.

Another aspect of the invention provides a method delivering a medication to the tissues of a laparoscopic port site wound, the method comprising the steps of: (a) providing an obturator sleeve in the form of an elongated tube configured to fittingly slide over the obturator, the sleeve comprising: (i) a proximal end, a distal end, an outer wall, and an inner wall, the inner wall forming a hollow passage for advancement of medical instruments through the sleeve; (ii) an internal flow passage for receiving a liquid medication, wherein the internal flow passage is located between the outer wall and the inner wall of the sleeve and between the proximal end and the distal end of the sleeve; (iii) a medication inlet for delivery of the liquid medication to the internal flow passage, wherein the medication inlet is located at the proximal end of the sleeve and is fluidly connected to the internal flow passage; (iv) a plurality of apertures located within the outer wall and opening into the internal flow passage; and (v) a diffusion polymer located within the internal flow passage for initially absorbing the liquid medication delivered into the internal flow passage and then releasing the absorbed medication through the apertures; (b) placing the obturator sleeve into a laparoscopic port site wound so that the outside surface of the sleeve contacts the tissue walls of the port site wound; and (c) delivering the liquid medication into the internal flow passage so that the medication passes through the diffusion polymer and out through the apertures to infiltrate the tissues of the port site wound, wherein the method provides even dissemination of the liquid medication to the fascia/muscle layers in which the majority of sensory and motor nerves of the lateral abdominal wall are located.

The liquid medication can be introduced into the internal flow passage manually such as with a syringe, or by way of a programmable pump. The medication can also be given as a burst dose, intermittently, or continuously during the laparoscopic procedure. The nature and advantages of the present invention will be more fully appreciated after reviewing the accompanying drawings, detailed description and claims.

BRIEF DESCRIPTION OF THE DRAWINGS

The accompanying drawings illustrate embodiments of the invention and, together with a general description of the invention given above, and the detailed description given below, serve to explain the principles of the invention.

DETAILED DESCRIPTION OF THE INVENTION

The present invention discloses embodiments of a device and method for infiltration of a liquid medication into the superficial and deep layers of a port site wound during a laparoscopic procedure. Typical liquid medications for use with the inventive devices and methods disclosed herein include, but are not limited to, local anesthetics such as bupivacaine and lidocaine, and other common post-operative medications including steroids such as dexamethasone, non-steroidal anti-inflammatory agents, and antibiotics.

Figure 1:
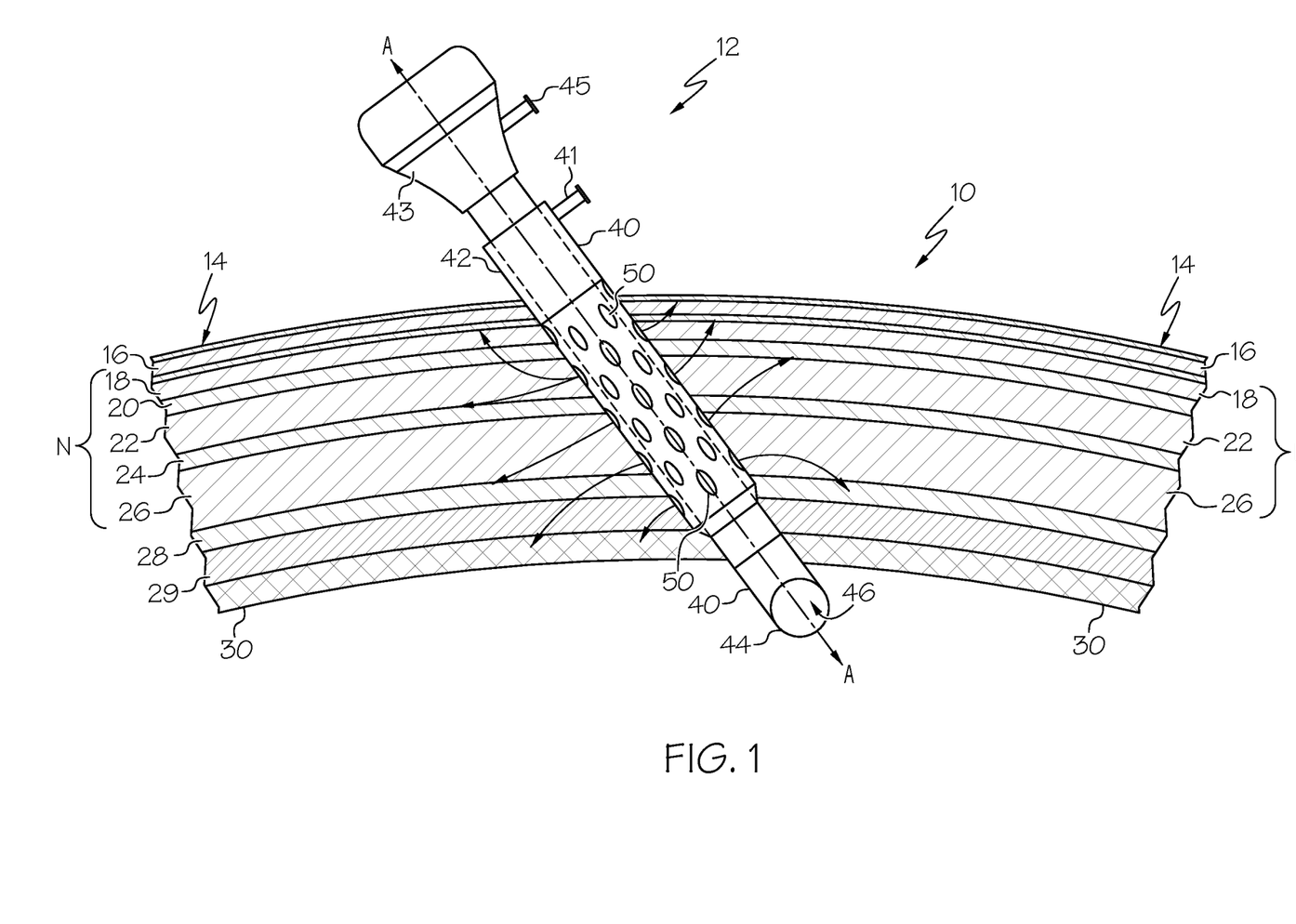
FIG. 1 is a cross-sectional view of one embodiment of a sleeve for a trocar assembly according to the present invention, after insertion through a port site wound created in the lateral abdominal wall of a patient.

FIG. 1 illustrates one embodiment of the present invention in the form of a trocar assembly 12 which is used to puncture the lateral abdominal wall 10 of a patient undergoing laparoscopic surgery. The trocar assembly includes a central obturator (not shown) and a hollow sleeve 40. The obturator can be any elongate object with a sharpened distal end, as known in the art, for safely puncturing the layers of the abdominal wall. The hollow sleeve 40 is an elongated tube configured to fittingly slide over the obturator during creation of the port site wound to access the intraperitoneal space. The obturator is then removed, while the sleeve 40 remains as a port or interface. The proximal or external end 42 of the sleeve 40 is typically attached to a conventional hub assembly 43 which has a $CO_2$ gas inlet 45, as shown. The hub 43 attaches to the sleeve 40 at its proximal end 42, and medical instruments can pass sequentially through the hub 43 and the hollow passage 46 to exit at the distal end 44 of the sleeve.

In FIG. 1, the dissemination of a liquid medication such as a local anesthetic is illustrated by arrows exiting a plurality of holes or apertures 50 in the sleeve 40. The sleeve 40 is anchored within the lateral abdominal wall 10 by the severed fascia/muscle tissue planes 14-30 forming the walls of the port site wound. More specifically, the sleeve 40 is shown following penetration at an angle through (in order) the skin 14, subcutaneous fat 16, the external oblique muscle 18, the external oblique fascia 20, the internal oblique muscle 22, the internal oblique fascia 24, the transversus abdominis muscle 26, the transversalis fascia 28, the pre-peritoneal fat 29 and the peritoneum 30 of the lateral abdominal wall. Although ideal for use in lateral abdominal wall 10 approaches to the peritoneal space, the inventive device and method disclosed herein can also be useful at other anatomic locations, such as the abdominal midline or the thorax.

The grouping of fascia and muscle layers indicated by the letter N in FIG. 1 specifies abdominal wall layers in which the majority of large sensory and motor nerves of the lateral abdominal wall are located. The layers containing large nerves include the external oblique muscle layer 18 through the transversus abdominis muscle layer 26 (i.e. layers 18-26). Infiltration of local anesthetic medication into these layers can not only anesthetize the severed nerve endings exposed along the tissue walls of the port site wound, but also can infiltrate layers N to reach undamaged branches of the iliohypogastric, ilioinguinal and thoraco-abdominal nerves running along and within the fascial planes.

Figure 2:
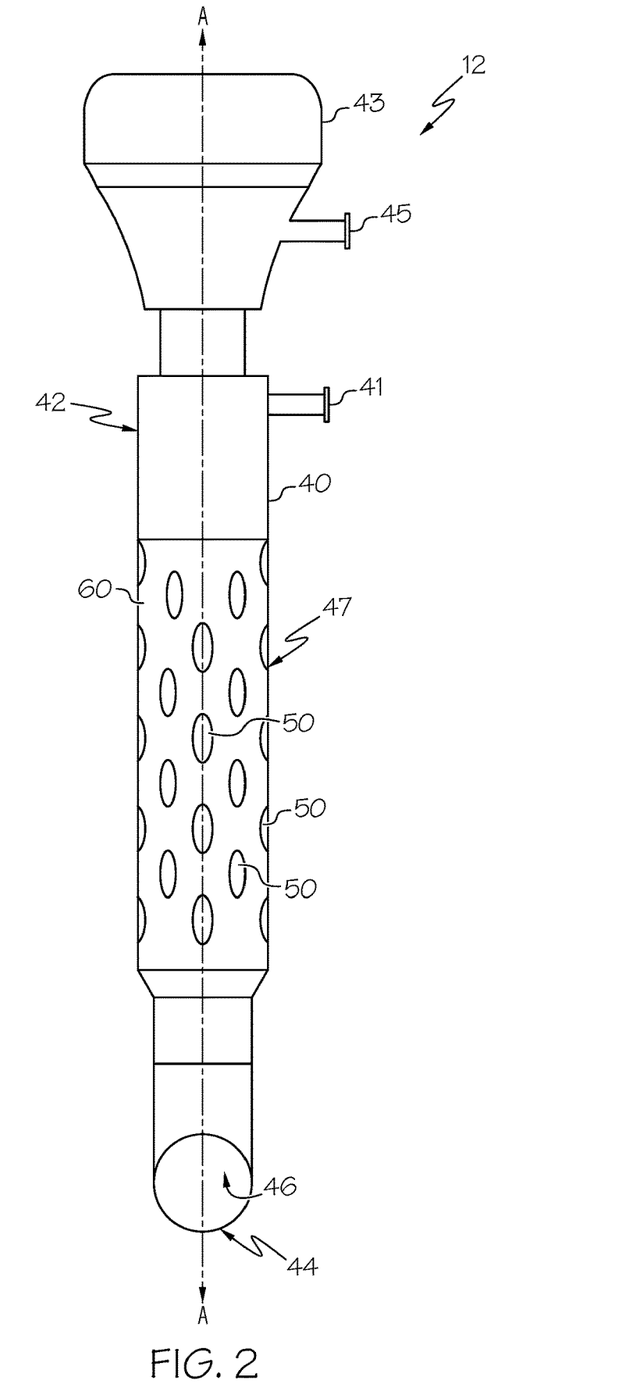
FIG. 2 is a perspective view of the sleeve for a trocar assembly of FIG. 1.
Figure 3:
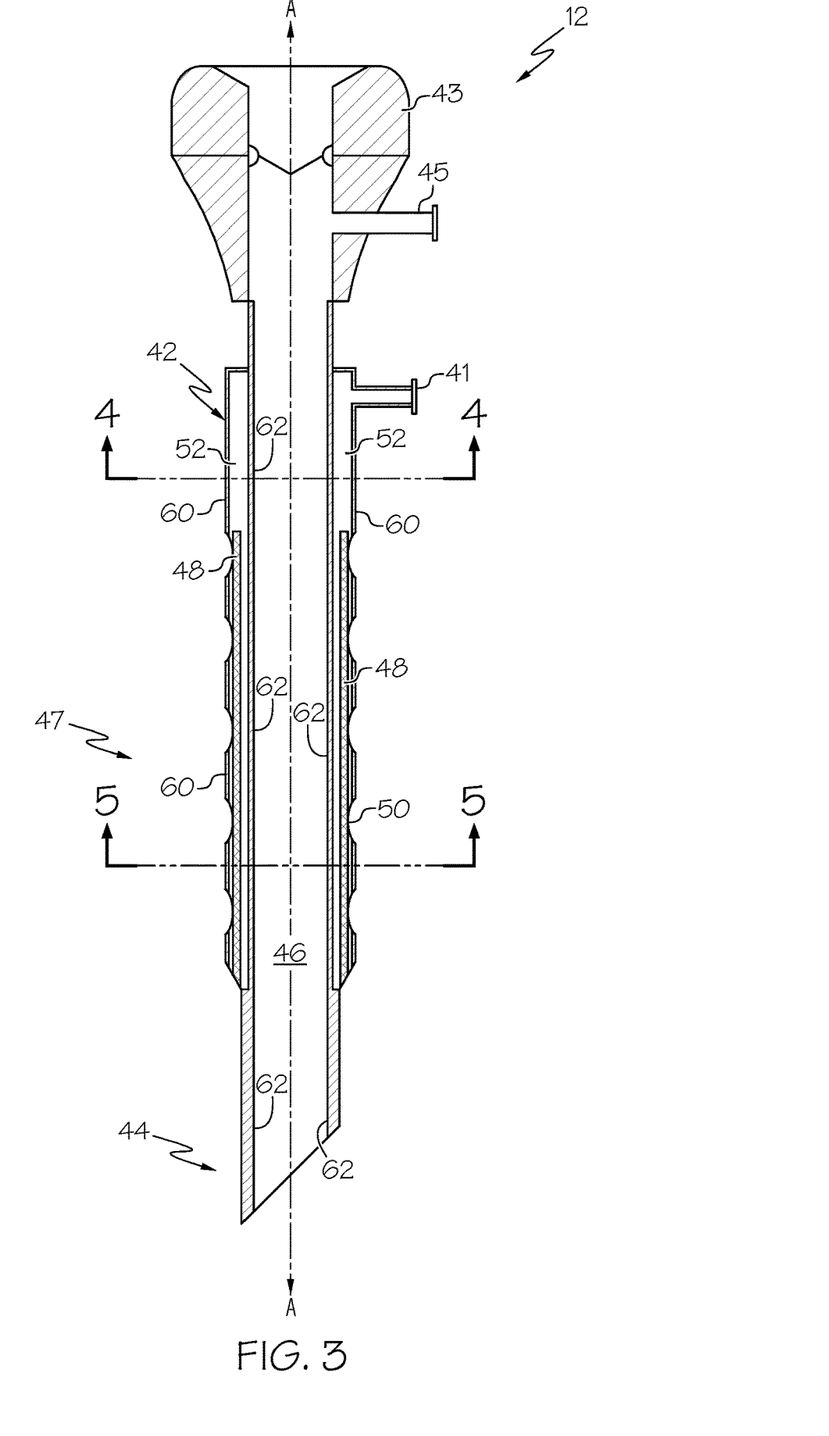
FIG. 3 is a sagittal cross-sectional view of the sleeve of FIG. 2.

As illustrated in FIGS. 1-3, the sleeve 40 includes a medication inlet 41 at its proximal end 42 in the form of a valve or luer lock. The medication inlet 41 is used for delivering liquid medication into the sleeve, and is fluidly connected to an internal flow passage 52 (see FIG. 3). FIG. 3 illustrates the internal flow passage 52 as a container for receiving liquid from the inlet 41. The internal flow passage 52 is located between an outer wall 60 and an inner wall 62, and runs longitudinally from the proximal end 42 to the distal end 44 of the sleeve. The hollow passage 46 is formed by the inner wall 62, and the apertures 50 serve as passageways through the outer wall 60. A second inlet, valve or luer lock (not shown) can also be included at the proximal end 42 to provide a means to release any increase in pressure that may develop inside the internal flow passage 52, for example, to relieve an increase in pressure caused by air injected/delivered with the liquid medication through the medication inlet 41.

As shown in FIGS. 2 and 3, the middle portion 47 of the sleeve includes the plurality of perforations or apertures 50 which allow passage of liquid medication out of the sleeve to infiltrate the surrounding tissues. It can be appreciated from viewing FIG. 3 that the internal flow passage 52, in the middle portion 47 of the sleeve, includes a material 48 referred to herein as a diffusion polymer 48. The diffusion polymer 48 is preferably a solid (i.e. rigid) or semi-solid (i.e. flexible) biocompatible material that is non-biodegradable, and can be provided as a single component, or as multiple sections for placement within the internal flow passage 52. The diffusion polymer 48 acts to reversibly absorb the liquid medication as it is delivered into the flow passage 52 through the inlet 41. Liquid medication is typically not released from the diffusion polymer 48 until physical contact is made between the diffusion polymer and the port site wound tissue. Since the sleeve 40 is anchored in the port site wound as noted above (see FIG. 1), during the surgical procedure the severed port site wound tissue will pass through the apertures 50 and make contact with the polymer 48.

Figure 6:
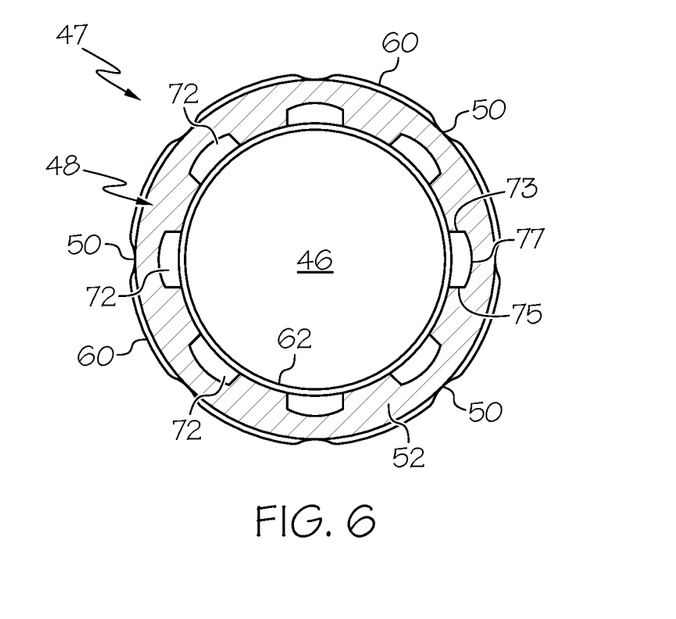
FIG. 6 is a top cross-sectional view through the middle portion of another embodiment of a sleeve for a trocar assembly according to the present invention.

The diffusion polymer 48 can be seated along the outside wall 60 of the internal flow passage 52, as shown in FIG. 3. The diffusion polymer 48 preferably does not degrade, expand, or change in size, and remains inside the internal flow passage 52 during use. The diffusion polymer 48 may be manufactured along with and included in the sleeve 40, or the polymer material may be shaped and inserted following the sleeve's manufacture. As shown in FIG. 6, the diffusion polymer 48 may incorporate a crenellated or otherwise contoured pattern in the form of multiple, regular, rectangular spaces. The spaced apart crenellations create a plurality of conduits or channels 72 within the flow passage 52, to provide uniform longitudinal distribution of the medication down the length of the sleeve.

The plurality of apertures 50 located within the outer wall 60 open into the internal flow passage 52 to expose the diffusion polymer 48 within. The apertures 50 need not be perfectly round, and may be ovoid, elliptical, or any suitable shape so long as they allow the passage or transport of fluids therethrough to the contacting wound tissue. The apertures 50 also need not be all the same size; indeed, apertures may be larger in the middle of the sleeve, larger proximally than distally, or vice versa as needed to specifically release more (or less) anesthetic medication over a period of time. In use, the liquid medication delivered through the inlet 41 preferably passes into the internal flow passage 52, through the diffusion polymer 48, and, when contact is made between the diffusion polymer 48 and the port site wound tissue, through the outer wall 60 of the sleeve via the plurality of apertures 50. Indeed, with use of the inventive sleeve 40, liquid medication can be steadily released (i.e. progressively, little by little) from the polymer 48 and through the apertures 50 to infiltrate the port site wound tissue.

Figure 4:
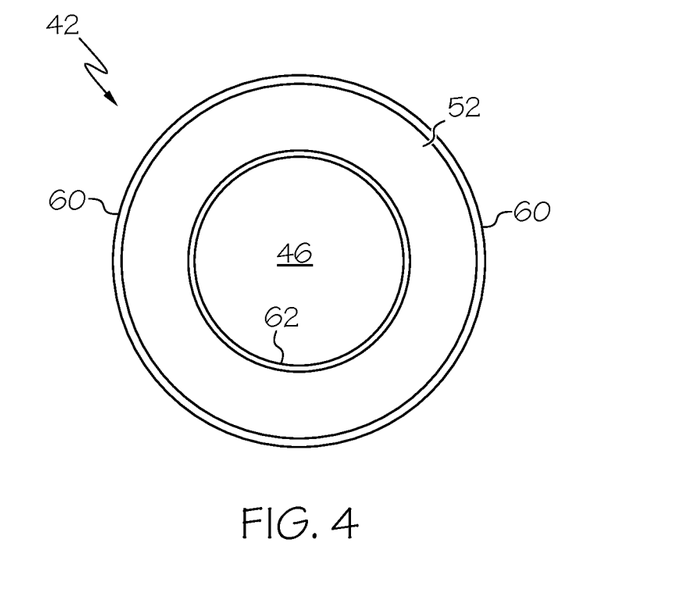
FIG. 4 is a top cross-sectional view through line 4-4 the sleeve of FIG. 3.
Figure 5:
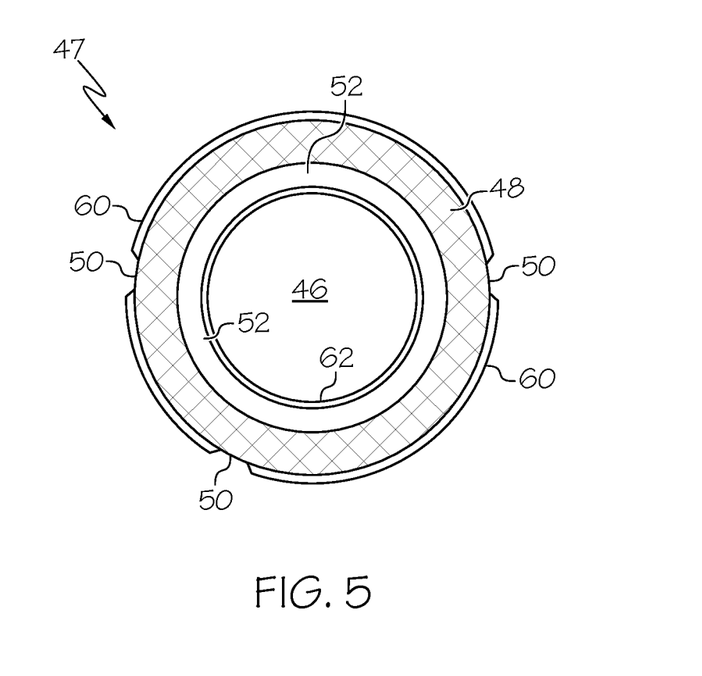
FIG. 5 is a top cross-sectional view through the middle portion, i.e. line 5-5, of the sleeve of FIG. 3.

FIGS. 4 and 5 are top cross-sectional views through lines 4-4 and 5-5 of FIG. 3, respectively, and illustrate cross-sectional differences between the proximal end 42 (FIG. 4) and the middle portion 47 (FIG. 5) of the sleeve. Specifically, looking at FIG. 4, the proximal end 42 of the sleeve includes the outer wall 60 and the inner wall 62, with the internal flow passage 52 present between the walls 60, 62 and the separate, hollow passage 46 extending longitudinally inside the inner wall 62. It can be appreciated from viewing FIG. 4 that the internal flow passage 52, formed between the inner and outer walls 60, 62, is distinct from hollow passage 46 which is formed by the inner circumference of the inner wall. In the middle portion 47 of the sleeve, as illustrated in FIG. 5, the internal flow passage 52 includes the diffusion polymer 48 seated within.

In the embodiment shown in FIG. 5 the internal flow passage 52 houses the diffusion polymer 48 and extends down the sleeve along the inner wall 62 towards the distal end 44 of the sleeve 40. The diffusion polymer 48 is shown in FIG. 5 hugging the outer circumference of the internal flow passage 52 so that it does not block the free flow of liquid medication down passage 52 to the distal end 44 of the sleeve. This ensures that the liquid medication is not preferentially absorbed at the proximal end 42 of the sleeve, allowing the liquid to be distributed uniformly along the length of the internal flow passage 52 and through the plurality of apertures 50. The inventive sleeve 40 is therefore designed to provide even dissemination of liquid medication out of the plurality of apertures 50 to the fascia/muscle layers in which the majority of sensory and motor nerves of the lateral abdominal wall are located (see grouped fascia/muscle layers N in FIG. 1).

In one embodiment, shown in FIG. 6, the internal flow passage 52 can include a plurality of distinct channels 72. These channels 72 are part of the internal flow passage 52 and thus receive fluid delivered through the inlet 41. As seen on cross-section, the channels 72 include a pair of side walls 73, 75 that project from the inner wall 62 into the flow passage 52, and a top wall 77. The channels 72 can prevent the diffusion polymer 48 from completely filling and "plugging" the internal flow passage 52, and therefore can serve as conduits for the liquid medication to pass freely down the length of the internal flow passage 52 without interference from the diffusion polymer 48.

The channels 72 shown in FIG. 6 can be created in different ways. In one embodiment (as noted above), the diffusion polymer 48 itself may be shaped to incorporate a crenellated or otherwise contoured pattern in the form of multiple, regular, rectangular spaces. The spaced apart crenellations form the side walls 73, 75 and top wall 77 of each channel 72, such that upon placement within the flow passage 52 the plurality of crenellations outline the plurality of channels 72 down the length of the flow passage 52. In another embodiment, the side walls 73, 75 of the channels 72 can be formed by physical extensions of the inner wall 62, projecting into the internal flow passage 52, and the top wall 77 can be a fenestrated cap joining the two side walls 73, 75. The fenestrations or holes in the top wall 77 can allow the liquid medication to pass through the channel 72 into the diffusion polymer 48. In either embodiment, the channels 72 provide for free flow of liquid medication down the length of the internal flow passage 52, so that the liquid can be uniformly distributed.

As noted above, the properties of the diffusion polymer 48 are such that there is controlled release of medication into the tissues; the absorbed liquid will not immediately pass through the polymer 48 and spill out through the apertures 50. Rather, the diffusion polymer 48 will release the absorbed medication only upon physical contact with the surrounding tissue of the port site wound. Contact with wound tissue causes the liquid to be released from the polymer and move into the tissues via passive diffusion. Specifically, the physical properties of the wound tissue serve to overcome the surface tension between the diffusion polymer 48 and the absorbed liquid medication, thereby freeing the medication from the diffusion polymer. The steady delivery of the liquid medication allows it to diffuse into and penetrate the tissues and nerves. This is particularly advantageous for local anesthetics, allowing them to infiltrate branches of the large sensory and motor nerves running through the fascial layers of the wound tissue (see layers N in FIG. 1) to provide prolonged anesthesia.

The inventive device and method of use can be used to uniformly, reliably and steadily disseminate liquid medication into the severed tissue and free nerve endings lining the port site wound, exactly along the path made during insertion of the obturator and its sleeve. As medication passes through the diffusion polymer 48 and out into the surrounding tissues, additional liquid medication can be delivered as needed through the inlet 41. This can be via a burst dose, intermittently, or continuously, and either by syringe or through use of a programmable pump. A burst dose of local anesthetic delivered through the apertures 50 prior to removing the trocar assembly can result in less break-through pain post-operatively. Similarly, a burst dose of a steroid such as dexamethasone can be administered through the sleeve to decrease the post-operative inflammatory process.

Forceful injection of liquid through the inlet 41 may transiently increase the rate of flow through the apertures 50, but will not result in vigorous, uncontrolled and/or voluminous outflow. Such brisk injection is buffered by the diffusion polymer 48, so that the forceful injection of liquid medication does not cause the liquid to rapidly flow down the outer surface of the sleeve and into the abdominal cavity. Indeed, whether a large volume of liquid is forcefully injected, or a small volume of liquid is delivered intermittently, following initial absorption by the polymer material there is generally a steady, controlled release of medication into the surrounding tissues at a substantially unvarying rate.

In addition, the inventive sleeve 40 can prevent uneven anesthesia of the port site wound tissue due to pooling of the liquid medication into the most gravity-dependent areas of the sleeve, as observed with prior art devices and methods. As noted above, medication is absorbed and then uniformly released from the diffusion polymer 48 through each of the plurality of apertures 50 at a controlled and steady rate, where it can adequately infiltrate, permeate, disseminate into and/or penetrate the interstices and openings of exposed biological tissues, such as the tissue walls of a port site wound. The steady release of medication can decrease the amount of intraoperative general anesthetic required, the amount of post-operative narcotic needed, and the incidence of breakthrough pain. The liquid medication can be delivered at maximum strength to the "actual" surgical site, both during the planned surgery and post-operatively, and not at an "intended site" prior to incision and obturator placement. The inventive device therefore provides the ability to place medication where and when it is needed most.

Pharmaceutically acceptable non-biodegradable materials for use as a diffusion polymer according to the present invention include polymers, textiles, foams, or other materials which are preferably FDA approved or GRAS (generally recognized as safe), and which must be able to reversibly absorb the desired liquid medication without chemically interacting with it. Examples of preferred non-biodegradable diffusion polymers include ethylene vinyl acetate, poly (ethylene vinyl acetate) (PEVA), poly(meth)acrylic acid, polymethyl methacrylate, polyamides, silicon and silicon-based polymers (such as polydimethylsiloxane or PDMS), copolymers and mixtures thereof. PEVA is the copolymer of ethylene and vinyl acetate, and has been used in the development of medical and controlled drug delivery devices by employing casting and freeze drying methods. PEVA-based devices are designed to slowly release drug compounds over a relatively long period of time. They are known to provoke no inflammatory responses and have good tissue compatibility.

The type of polymer material employed in the sleeve can differ, depending on whether there is a need for a fast rate or slow rate of delivery of the liquid medication. For example, PEVA is readily available with a variety of vinyl acetate contents, ranging from 0% to 40%. The permeability of these copolymer films changes substantially with varying vinyl acetate content, and thus it is possible to tailor the release rate to a desired value by slightly changing the polymer composition. The chemical properties and parameters of the polymer, material such as diffusion and permeability, can provide a diffusion coefficient for the liquid medication at a specific temperature and concentration. Diffusivity or diffusion coefficient is a proportionality constant between molecular diffusion of the liquid medication and the concentration gradient of the liquid within the polymer (or the driving force for diffusion). Diffusivity is encountered in Fick's law and numerous other equations of physical chemistry. This can be determined thru mathematical models, and can be beneficial in polymer material design. For example, the thickness or mass of the diffusion polymer material can be adjusted depending on need, therefore providing the ability to control how the liquid medication (such as bupivacaine, other local anesthetics, NSAIDS, steroids, and combinations thereof) interacts with the diffusion polymer and effects the rate of release of medication from the polymer to the tissues.

For example, if the planned surgical procedure is expected to last a long time such as 3 or more hours, and a liquid local anesthetic medication such as bupivacaine is to be used, the diffusion polymer can be selected to include properties which slowly release the absorbed bupivacaine to the tissues. In contrast, for short surgical procedures the diffusion polymer material can be selected to include properties which releases the medication to the tissues more easily/quickly. The diffusion polymer may also be a combination of materials, which together deliver the medication to the apertures at a rate appropriate for the planned operative procedure. The diffusion polymer may also be a coated substrate that provides the desired chemical and physical properties needed to deliver the medication to the tissues. Examples include but are not limited a polymer-coated cotton, polymer-impregnated foam, or other suitable combination of materials known in the art.

In addition to varying the type of polymer used, since flow rate is directly proportional to the cross-sectional area of the apertures, the sleeve can be designed so that, depending on the length of the planned surgery, medication can be delivered through the apertures at a desired rate. More specifically, apertures having a small surface area can be used when slow release of medication is desired, which is useful for long procedures, while larger apertures will release more local anesthetic over a short period of time, and can be used for short surgical procedures. In either manner, the conventional prior art practice noted above in which the surgeon must remember to timely inject medication into the port site wound, both prior to and near the conclusion of the procedure, can be eliminated.

An illustrative, non-limiting range for sleeve porosity, based on the percentage of open area provided by the apertures 50 to the total surface area of the sleeve 40, can be from about 10% to about 80%, and more preferably from about 20% to about 50%, depending on the surgical requirements. The apertures 50 preferably have a diameter of at least about 0.5 mm for satisfactory drug distribution and flushing. In a preferred embodiment, the apertures have a diameter of between about 1.0 mm and 5.0 mm for long procedures (i.e. longer than 1 hour) and between about 0.5 mm and 1.5 mm for short procedures (i.e. shorter than an hour).

As noted above, the grouping indicated by N in FIG. 1 indicates the fascia/muscle layers 18-26, in which the majority of large sensory and motor nerves of the lateral abdominal wall are located, notably the ilio-hypogastric and ilio-inguinal nerves, as well as the thoraco-abdominal sensory nerves. Most of these large nerves have smaller branches that spread out and perforate the fascial layers above them as they advance toward the skin surface. The inventive device and method can provide prolonged infiltration of medication to these deeper tissue layers N, and thus deposit more medication around large sensory nerves from which the free nerve endings of the port site wound originate. Thus, infiltration of these fascial layers can advantageously result in a "distal nerve block", with local anesthetic affecting distribution of these large nerves beyond the free nerve endings of the port site location, and resulting in better pain control.

In use, the sleeve can be initially loaded with liquid medication in the operating room by the surgeon or other medical professional via syringe delivery through the medication inlet. Alternatively, the sleeve can be pre-loaded with medication during its manufacture, as well as prior to sale and/or use. To enhance the rate of steady delivery of the medication through the sleeve intraoperatively, once the liquid medication is present in the internal flow passage of the sleeve the surgeon can subsequently inject a small amount of air (i.e. 1-2 cc) into the medication inlet via a syringe, and then close the inlet, e.g. via a luer lock mechanism. This can effectively pressurize the sleeve's internal flow passage 52 and the diffusion polymer 48, which does not cause an immediate rush of liquid medication to the wound tissue but can transiently increase the rate of passage of medication through the apertures 50. The invention further envisions systems in which a pressure gauge can be applied at the inlet 41 when continuous intra-operative administration of local anesthetic medication through the sleeve is planned.

The inventive sleeve can include a distal marker (not shown) indicating where medication dispensing begins, so that the surgeon does not attempt to advance the marker into the abdominal cavity. Nevertheless, in the event that there is advanced placement of the sleeve into the abdominal cavity, the inventive sleeve beneficially will not spill its medicinal contents out of the apertures and into the abdominal cavity because of the diffusion polymer. It is thus advantageous to provide the diffusion polymer as described herein, which will only release its absorbed medication if presented with tissue contact from the port site wound. For example, should a prior art anesthetic sleeve having no internal diffusion polymer to absorb the medication were to be used in this situation (advancement of the obturator sleeve into the abdominal cavity), injection of liquid medication into the sleeve will rapidly exit the sleeve and spill into the abdominal cavity. In contrast, the inventive sleeve will not allow such leakage of liquid medication into the abdominal cavity.

While the present invention is illustrated by the description of particular embodiments in considerable detail, such detail is not intended to restrict or limit the scope of the appended claims. Additional advantages and modifications will be readily apparent to those skilled in the art without departing from the concept or scope of the invention.

What is claimed is:

1. An obturator sleeve for delivery of a liquid medication along the path of a port site wound during a laparoscopic procedure, wherein the sleeve is an elongated tube comprising:
   a) a proximal end, a distal end, an outer wall, and an inner wall, the inner wall forming a hollow passage for advancement of medical instruments through the sleeve;
   b) an internal flow passage for receiving a liquid medication, wherein the internal flow passage is located between the outer wall and the inner wall of the sleeve and between the proximal end and the distal end of the sleeve;
   c) a medication inlet for delivery of the liquid medication to the internal flow passage, wherein the medication inlet is located at the proximal end of the sleeve and is fluidly connected to the internal flow passage;
   d) a plurality of apertures located within the outer wall and opening into the internal flow passage; and
   e) a diffusion polymer located within the internal flow passage for initially absorbing the liquid medication delivered into the internal flow passage and then releasing the absorbed medication through the apertures, wherein a plurality of channels is formed along the length of the internal flow passage, each of the plurality of channels including two side walls projecting from the inner wall into the internal flow passage and a top wall joining the two side walls, each top wall including fenestrations which allow the liquid medication to pass into the diffusion polymer.

2. The obturator sleeve of claim 1, wherein the diffusion polymer does not release the absorbed liquid medication until physical contact is made with port site wound tissue within the apertures.

3. The obturator sleeve of claim 1, wherein the liquid medication is a local anesthetic, a steroid, a non-steroidal anti-inflammatory agent, an antibiotic, or combinations thereof.

4. The obturator sleeve of claim 1, wherein the sleeve is a component of a trocar assembly, the trocar assembly further comprising an obturator for creating a port site wound by puncturing the abdominal wall of a patient undergoing a laparoscopic procedure, the sleeve configured to fittingly slide over the obturator during creation of the port site wound, and wherein medical instruments may be advanced through the sleeve after removal of the obturator.

5. The obturator sleeve of claim 4, wherein the trocar assembly further comprises a hub assembly including a gas inlet capable of connection to a $CO_2$ gas supply, wherein the hub assembly attaches to the proximal end of the sleeve and medical instruments can pass sequentially through the hub and the hollow passage of the sleeve.

6. The obturator sleeve of claim 1, wherein each of the plurality of apertures has a diameter between about 1.0 mm and 5.0 mm.

7. The obturator sleeve of claim 1, wherein each of the plurality of apertures has a diameter between about 0.5 mm and 1.5 mm.

8. A trocar assembly for delivery of a liquid medication along the path of a port site wound during a laparoscopic procedure, the assembly comprising:
   a) an obturator for creating a port site wound by puncturing the abdominal wall of a patient undergoing a laparoscopic procedure; and
   b) an obturator sleeve in the form of an elongated tube configured to fittingly slide over the obturator, the sleeve comprising:
      i) a proximal end, a distal end, an outer wall, and an inner wall, the inner wall forming a hollow passage for advancement of medical instruments through the sleeve;
      ii) an internal flow passage for receiving a liquid medication, wherein the internal flow passage is located between the outer wall and the inner wall of the sleeve and between the proximal end and the distal end of the sleeve;
      iii) a medication inlet for delivery of the liquid medication to the internal flow passage, wherein the medication inlet is located at the proximal end of the sleeve and is fluidly connected to the internal flow passage;
      iv) a plurality of apertures located within the outer wall and opening into the internal flow passage; and
      v) a diffusion polymer located within the internal flow passage for initially absorbing the liquid medication delivered into the internal flow passage and then releasing the absorbed medication through the apertures, wherein a plurality of channels is formed along the length of the internal flow passage, each of the plurality of channels including two side walls projecting from the inner wall into the internal flow passage and a top wall joining the two side walls, each top wall including fenestrations which allow the liquid medication to pass into the diffusion polymer, and wherein the released medication infiltrates the tissues of the port site wound.

9. The trocar assembly of claim 8, wherein the diffusion polymer does not release the absorbed liquid medication until physical contact is made with port site wound tissue within the apertures.

10. The trocar assembly of claim 8, wherein the medication is a local anesthetic, a steroid, a non-steroidal anti-inflammatory agent, an antibiotic, or combinations thereof.

11. A method for delivering a medication to the tissues of a laparoscopic port site wound, the method comprising the steps of:
    a) providing an obturator sleeve in the form of an elongated tube configured to fittingly slide over the obturator, the sleeve comprising:
       i) a proximal end, a distal end, an outer wall, and an inner wall, the inner wall forming a hollow passage for advancement of medical instruments through the sleeve;
       ii) an internal flow passage for receiving a liquid medication, wherein the internal flow passage is located between the outer wall and the inner wall of the sleeve and between the proximal end and the distal end of the sleeve;
       iii) a medication inlet for delivery of the liquid medication to the internal flow passage, wherein the medication inlet is located at the proximal end of the sleeve and is fluidly connected to the internal flow passage;

iv) a plurality of apertures located within the outer wall and opening into the internal flow passage; and v) a diffusion polymer located within the internal flow passage for initially absorbing the liquid medication delivered into the internal flow passage and then releasing the absorbed medication through the apertures;

b) placing the obturator sleeve into a laparoscopic port site wound so that the outside surface of the sleeve contacts the tissue walls of the port site wound; and c) delivering the liquid medication into the internal flow passage so that the medication passes through the diffusion polymer and out through the apertures to infiltrate the tissues of the port site wound, wherein the method provides even dissemination of the liquid medication to the fascia/muscle layers in which the majority of sensory and motor nerves of the lateral abdominal wall are located.

12. The method of claim 11, wherein the step of delivering the liquid medication is performed intermittently during the laparoscopic procedure.

13. The method of claim 11, wherein the step of delivering the liquid medication is performed continuously during the laparoscopic procedure.

14. The method of claim 11, wherein the step of delivering the liquid medication is performed by programmable pump.

15. The method of claim 11, wherein the step of delivering the liquid medication is performed as a single burst dose.

16. The method of claim 11, further comprising the step of:

c) injecting air into the internal flow passage following the step of delivering the liquid medication, in order to increase the rate passage of medication through the apertures.

17. The method of claim 11, wherein the liquid medication is a local anesthetic, a steroid, a non-steroidal anti-inflammatory agent, an antibiotic, or combinations thereof.

18. The method of claim 11, wherein the absorbed liquid medication is not released from the diffusion polymer until physical contact of the diffusion polymer is made with wound tissue within the apertures.

* * * * *